US00PP31221P2

(12) United States Plant Patent
Hansen

(10) Patent No.: US PP31,221 P2
(45) Date of Patent: Dec. 10, 2019

(54) ***HEUCHERA* PLANT NAMED 'APPLE TWIST'**

(50) Latin Name: ***Heuchera* hybrid**
Varietal Denomination: Apple Twist

(71) Applicant: Hans A Hansen, Zeeland, MI (US)

(72) Inventor: Hans A Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 16/350,493

(22) Filed: Nov. 21, 2018

(51) Int. Cl.
*A01H 5/12* (2018.01)
*A01H 6/80* (2018.01)

(52) U.S. Cl.
USPC ..... Plt./440

(58) Field of Classification Search
USPC ..... Plt./263.1, 440
See application file for complete search history.

*Primary Examiner* — Susan McCormick Ewoldt
*Assistant Examiner* — Karen M Redden

(57) ABSTRACT

The new and distinct hybrid of *Heuchera* plant named 'Apple Twist' with medium sinuate margined foliage with rounded apices and lobes. The spring leaf blades begin the reddish bronze between the veins and later mature to an apple green with random silver overlay between the veins. Branched panicles produce creamy green floral effect for about five weeks in mid-summer. The new plant is vigorous and produces large clumps with many large leaves.

1 Drawing Sheet

Botanical denomination: *Heuchera* hybrid.
Variety denomination: 'Apple Twist'.

STATEMENT REGARDING PRIOR DISCLOSURES UNDER 37 CFR 1.77(b)(6)

The first public disclosure of the claimed plant, in the form of a sale, was made by Walters Gardens, Inc. on Mar. 28, 2018. Prior to that, on Dec. 1, 2017 the claimed plant was displayed with a photograph and brief description in a website operated by Walters Gardens, Inc., who obtained the plant and all information relating thereto, from the inventor. No plants of *Heuchera* 'Apple Twist' have been sold, in this country or anywhere in the world, nor has any disclosure of the new plant been made, more than one year prior the filing date of this application, and such sale or disclosure within one year was either derived directly or indirectly from the inventor.

BACKGROUND OF THE INVENTION

The present invention relates to a new and distinct cultivar of Coral Bells in the Saxifragaceae family and given the cultivar name of 'Apple Twist'. *Heuchera* 'Apple Twist' was hybridized by the inventor on Mar. 8, 2013 at a wholesale perennial nursery in Zeeland, Mich., USA. The seed or female parent was the proprietary unreleased hybrid known as 'Making Waves' (not patented) and the pollen or male parent was the proprietary selection known as 'Malachite One' (not patented).

*Heuchera* 'Apple Twist' was first selected in the fall of 2015 and passed final evaluation in the fall of 2016 from among many other seedlings from the same cross and hundreds of other crosses and assigned the breeder code 13-302-8 through the remaining evaluation process. *Heuchera* 'Apple Twist' has been asexually propagated by division at the same nursery in Zeeland, Mich. in 2016 and by sterile, shoot-tip, tissue culture propagation, and the resultant plants have remained stable and continued to exhibit the same characteristics as the original plant for multiple generations.

BRIEF SUMMARY OF THE INVENTION

The nearest comparison varieties include: 'Appletini' U.S. Plant Pat. No. 29,396, 'Pretty Pistachio' U.S. Plant Pat. No. 29,361, 'Twist of Lime' U.S. Plant Pat. No. 30,618, 'Lemon Love' U.S. Plant patent application Ser. No. 15/998,375, 'Pear Crisp' U.S. Plant Pat. No. 23,568 and 'You're So Vein' Provisional U.S. Plant Patent Application No. 62/710,111. The male parent, 'Malachite One' has smaller, ruffled, green foliage without silver marbling. The female parent, 'Making Waves' has heavy sinuate margins and the foliage is more caramel-colored with near white flowers. 'Appletini' has darker chartreuse foliage with less silver marbling and does not display the reddish bronze in the spring foliage and the flowers are deep red. 'Pretty Pistachio' has larger chartreuse foliage without the reddish-bronze spring display and the flowers are raspberry-colored. 'Twist of Lime' brighter yellowish foliage without the reddish-bronze spring display and the flowers are smaller and creamy white. 'Lemon Love' has brighter and more yellow foliage without the spring reddish-bronze effect. 'Pear Crisp' is smaller in habit, the leaves are smaller, the lobes are acute and it does not develop the reddish bronze color. 'You're So Vein' has flatter foliage with bright pink flowers and the bronze spring effect is not as bright or reddish tinted. '*Heuchera* 'Apple Twist' differs from its parents as well as all other coral bells known to the applicant in the following combined traits:

1. Medium, rounded, sinuate-margined foliage with apices rounded and minutely apiculate.
2. Spring leaves produce reddish bronze between the veins.
3. Mature leaf color is apple green in part shade.
4. Leaf blades are shallowly dissected.

5. Flower effect is pale creamy green for five weeks in mid-summer.
6. The new plant is vigorous and produces medium dense clumps and many individual leaves.

BRIEF DESCRIPTION OF THE DRAWINGS

The photographs of the new plant demonstrate the overall appearance of the plant including the unique traits of the new plant in in Zeeland, Mich. The colors are as accurate as reasonably possible with color reproductions. Some slight variation of color may occur as a result of lighting quality, intensity, wavelength, and direction or reflection.

DETAILED BOTANICAL DESCRIPTION

Figure 1:
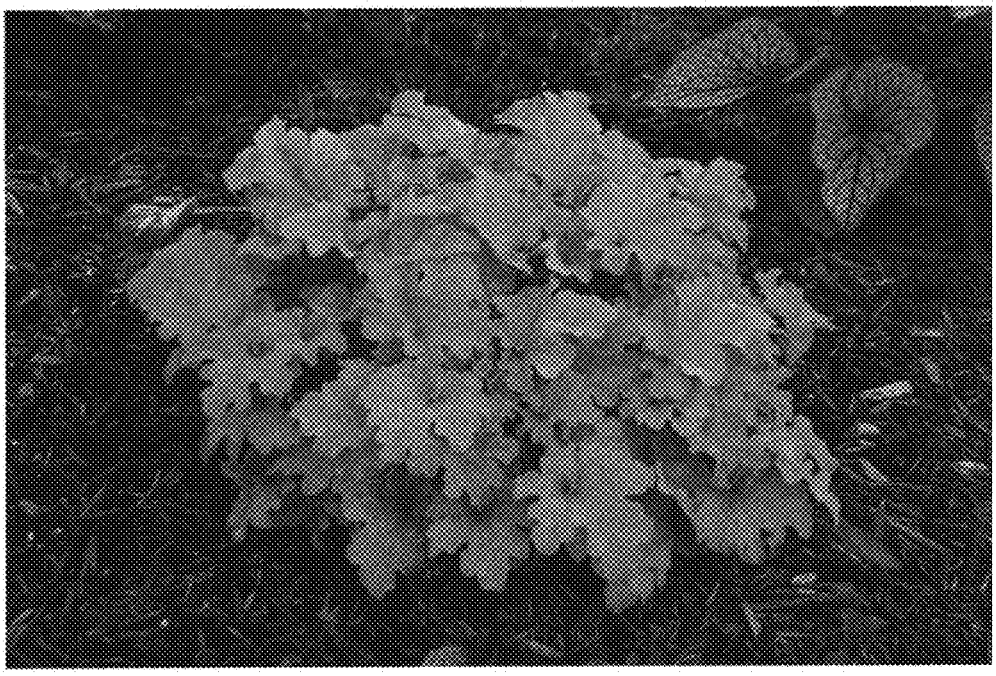
FIG. 1 shows a two-year-old plant prior to flowering season in a trial garden.
Figure 2:
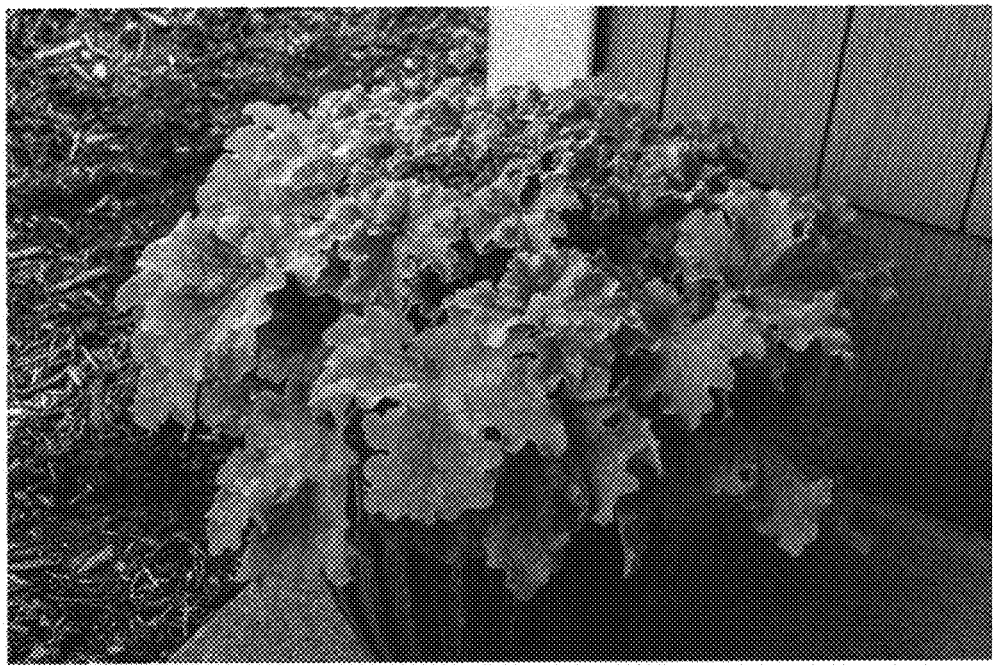
FIG. 2 shows a greenhouse-grown, two-year-old plant in early spring with reddish bronze developed on foliage between veins.

The following description is based on a two-year-old plant growing in a partially shaded greenhouse in Zeeland, Mich., USA. The new plant has not been grown under all possible environments and may phenotypically appear different under different conditions such as light, temperatures, fertilizer, and water, without any difference in genotype. The color descriptions used are from the 2015 edition of The Royal Horticultural Society Colour Chart except where common dictionary terms are used.

Parentage: Female or seed parent was the proprietary, unreleased hybrid known as 'Making Waves'; the male or pollen parent was 'Malachite One';

Plant habit: Hardy herbaceous perennial with basal rosette of foliage; mounded foliage about 24.0 cm tall and 54.0 cm in diameter, with scapes to about 50.0 cm long; with 11 stems per plant to about 1.5 cm long and 1.0 cm diameter at base, about 28 leaves per stem;

Roots: Fibrous, finely branched;

Growth rate: Rapid, rooting from cutting in two weeks and finishing in three-liter container in about two and a half months;

Foliage: Rounded; apex and lobe apices rounded and minutely apiculate; base cordate with basal lobes frequently overlapping to about 1.0 cm; margins crenate, ciliolate, mucronulate; micro-puberulent adaxial and pubescent abaxial; palmately shallowly lobed with five main lobes dissected less than one-third of the way to petiole; lustrous adaxial and matte abaxial; held nearly horizontal; margin sinuate at maturity and more sinuate as expanding;

Leaf blade size: To about 12.0 cm wide and 13.0 cm long, average about 9.5 cm wide and 10.2 cm long;

Leaf color: Spring and young emerging leaves adaxial and abaxial center nearest RHS 145B and adaxial and abaxial margin nearest RHS 145A, adaxial developing reddish-bronze between RHS 174A and RHS 174B between the veins; mature mid-season leaves adaxial nearest blend of RHS 144A and RHS 146D with marbling nearest RHS 194C, abaxial mature mid-season leaves nearest RHS 148C; fall and winter color adaxial nearest RHS 138A toward petiole and surrounding distal veins, nearest RHS 193B between distal veins; fall and winter color abaxial nearest RHS 147D;

Leaf quantity: Dense, about 300 per plant;

Veins: Palmate, hirsutulous abaxial and puberulent adaxial; costate abaxial, slightly impressed to nearly flat adaxial;

Vein color: Emerging or early spring adaxial nearest RHS 157A with emerging spring abaxial nearest RHS94D; mid-season and flowering time adaxial nearest RHS 145C in basal region near petiole and distally becoming nearest RHS 144A to RHS 146D, mid-season, mid-season and flowering time abaxial main veins nearest RHS 145D and secondary veins nearest RHS 146C; fall adaxial nearest RHS 147D toward petiole and distally becoming nearest RHS 138A, fall abaxial midrib base nearest 160C with distal and secondary veins becoming nearest RHS 146D;

Petiole: Cylindrical; base amplexicaul; with sparse pubescent hairs to about 2.0 mm long; to about 19.5 cm long and 3.0 mm wide above base stipules, average about 16.5 cm long and about 3.0 mm diameter above stipule;

Petiole color: Emerging leaf nearest RHS 145C; flowering season mature leaf nearest RHS 145A;

Stipule: Flared at base of petiole; glaucous and glabrous abaxial and adaxial; margin ciliate; to about 18.0 mm long and about 10.0 mm wide at base; with two lateral projections of about 2.0 mm long in distal portion;

Stipule color: Young expanding leaf adaxial and abaxial nearest RHS 145C; mature leaf adaxial and abaxial nearest RHS 145D;

Peduncle: Branched panicle; cylindrical; stiff; pubescent; upright; with short branches; to about 50.0 cm long and 4.5 mm diameter at base, average about 47.0 cm tall and 4.0 mm diameter; about 4 per plant with up to about 158 flowers per panicle, average about 145; tightly-branched panicle with up to 12 branches up to 7.2 cm long and 1.0 mm diameter decreasing distally, average 10 branches per panicle; lower branches mostly upright becoming drooping distally; with peduncle bracts subtending branches; flower density light;

Peduncle color: Nearest RHS 142C proximally and nearest RHS 145B distally;

Pedicel: Cylindrical, pubescent; about 2.0 mm long and 0.5 mm diameter; attitude outwardly to drooping;

Peduncle bracts: Palmate; sessile to petiolate; serrate to incised margins; apices and lobes acute; base attenuate; to 2.5 cm long and 2.0 cm across, decreasing distally;

Peduncle bract color: Adaxial and abaxial nearest RHS 145A,

Pedicel color: Nearest RHS 157C;

Flowering longevity: Panicle effective for about four to five weeks; individual flowers about 5 days; self-cleaning;

Buds one day prior to opening: Oblong ellipsoidal; rounded apex and attenuate base; puberulent to glandular; about 3.5 mm long and 2.5 mm diameter;

Bud color one day prior to opening: Nearest RHS 145D;

Flower: Perfect; campanulate; actinomorphic; about 6.0 mm long to tip of exserted style and 3.0 mm in diameter at corolla face;

Flower attitude: Drooping;

Calyx: Five, apex rounded, base fused in proximal 2.5 mm to form hypanthium; puberulent to glandular abaxial, glabrous adaxial; about 3.0 mm long and 2.5 mm wide at apex;

Sepals: Five; oblanceolate; rounded apex, fused in basal 2.0 mm; to about 3.0 mm long and 1.5 mm wide at fusion;

Sepal color: Abaxial lighter than RHS 157D, adaxial lighter than RHS 157D proximally and nearest RHS 145B distally;

Petals: Five; oblanceolate to spatulate; acute apex and attenuate base; entire; glabrous abaxial; micro-puberulent adaxial base; about 2.5 mm long and 1.0 mm wide in middle;

Petal color: Abaxial and adaxial nearest RHS NN155D;

Androecium: Five adnate to adaxial sepal about 1.0 mm above base;

*Filaments*.—Five, thin, glabrous, cylindrical; about 1.0 mm long and about 0.2 mm diameter; color lighter than RHS 157D.

*Anthers*.—Ellipsoidal, distinct, basifixed, longitudinal; about 0.7 mm long and about 0.2 mm across; color nearest RHS 157D.

*Pollen*.—Not observed.

Gynoecium: One, two-beaked; half-inferior; bifid style with pistil split at ovary; about 6.0 mm long and 3.0 mm across at base;

*Style*.—Bifid above ovary apex; about 3.0 mm long and about 0.5 mm diameter; color nearest RHS NN155B.

*Stigma*.—Acute apex, about 0.2 mm diameter; color nearest RHS NN155B.

*Ovary*.—Half-inferior, about 3.0 mm long and 1.5 mm diameter; acute apex, base rounded; color nearest RHS 145C.

Fruit and seeds: Not observed;

Disease and pest tolerance: The new plant grows best with ample moisture and drainage in either part sun or full shade. Cold hardy from USDA zones 4 to 9. Other resistance and tolerance outside of that normal for *Heuchera* is not known.

It is claimed:

1. The new and distinct coral bells plant named *Heuchera* 'Apple Twist' as herein described and illustrated.

* * * * *